(12) United States Patent
Schintz et al.

(10) Patent No.: US 6,641,048 B1
(45) Date of Patent: Nov. 4, 2003

(54) WINGED WRISTBAND

(75) Inventors: Michael Schintz, Swedesboro, NJ (US); Frank Gill, Smithtown, NY (US)

(73) Assignee: The Standard Register Company, Dayton, OH (US)

( * ) Notice: Subject to any disclaimer, the term of this patent is extended or adjusted under 35 U.S.C. 154(b) by 0 days.

(21) Appl. No.: 10/192,892

(22) Filed: Jul. 11, 2002

(51) Int. Cl.$^7$ ................................................. G06F 19/00
(52) U.S. Cl. ...................................... 235/487; 235/375
(58) Field of Search .................... 235/375, 487

(56) References Cited

U.S. PATENT DOCUMENTS

| | | |
|---|---|---|
| 3,197,899 A | 8/1965 | Twentier |
| 4,122,947 A | 10/1978 | Falla |
| 4,314,415 A | 2/1982 | De Woskin |
| 4,682,431 A | 7/1987 | Kowalchuk |
| 4,906,025 A | 3/1990 | Schreindl |
| 4,956,931 A | 9/1990 | Selke |
| 4,991,337 A | 2/1991 | Solon |
| 5,026,084 A | 6/1991 | Pasfield |
| 5,311,689 A | 5/1994 | Lindsey |
| 5,328,208 A | 7/1994 | Garrison |
| 5,364,133 A | 11/1994 | Hofer et al. |
| 5,457,906 A | 10/1995 | Mosher, Jr. |
| 5,653,472 A | 8/1997 | Huddleston et al. |
| 5,792,299 A | 8/1998 | Mosher, Jr. |
| 5,933,993 A | 8/1999 | Riley |
| 5,967,559 A | 10/1999 | Abramowitz |
| 6,000,160 A | 12/1999 | Riley |
| 6,016,618 A | 1/2000 | Attia et al. |
| 6,067,739 A | 5/2000 | Riley |
| 6,510,634 B1 * | 1/2003 | Riley ......................... 235/375 |

* cited by examiner

Primary Examiner—Harold I. Pitts
(74) Attorney, Agent, or Firm—Killworth, Gottman, Hagan & Schaeff LLP

(57) ABSTRACT

An elongate strip formable into a wristband. The elongate strip includes adhesive contact portions and one or more laterally-placed adhesive winged detents such that upon looped formation of the wristband, an adhesive bond is formed at the contact portions, and the detents can be folded over one or more parts of the elongate strip to provide enhanced wristband durability. In one configuration, a multiply sheet is defined by an elongate strip formable into a wristband and an array of labels, all die cut into a first ply adhesively removable from a second ply. The sheet can be either an individual cut sheet, part of a continuous fan-folded form or part of a larger continuous roll, any of which can be fed into a conventional automated printer to facilitate the placing of printed indicia on the wristband and labels.

37 Claims, 15 Drawing Sheets

WINGED WRISTBAND

BACKGROUND OF THE INVENTION

The present invention is directed generally to a printable form that includes detachable cut-outs formable into a wristband, and more particularly to a wristband with one or more detents on or near at least one end thereof that permit a more secure connection between joined ends upon wristband formation.

Upon admission to a hospital, a patient typically provides pertinent background information, such as patient name, social security number, primary physician, health insurance coverage, allergies and related known health history, and the nature of the ailment, just to name a few. Prior to the advent of electronic data processing and printing equipment, such information would be manually written or typed, then transcribed to a bracelet that could be placed on a patient's extremity, such as wrist or ankle, for ease of identification by treating hospital personnel. Errors in transcription and legibility of the printed indicia on the wristband could result in incorrect identification of vital patient information, thus compromising patient care. The availability of modern computing and printing equipment in virtually all hospitals and related health care facilities has significantly reduced the likelihood of such errors occurring, as information entered into the hospital database is automatically processed and printed directly onto a sheet-like form that includes an elongate strip that can be formed into a wristband. Simultaneously, some or all of the same information provided by the patient upon admission can be printed onto labels situated on the same form. The form is typically made from multiple plies, where the top (or face) ply capable of accepting printing thereon is adhesively bonded to a release layer (such as a conventional silicone coating) disposed on a liner ply. Cut-outs defined in the face ply permit easy removal of the elongate strip or labels from the liner ply of the form. Locations on the elongate strip (such as the ends) may have exposed pressure sensitive adhesive (PSA) that can be used to establish adhesive bracelet-forming contact. Hospital personnel generally secure the bracelet to the patient so that chances for misidentification of the patient are minimized. This is especially useful when, due to the patient's age or condition, verifying information cannot be readily ascertained by hospital personnel. An example of a form with cut-outs for labels and wristbands that can be fed into a printer to accept patient-unique information is U.S. Pat. No. 5,653,472 to Huddleston et al., owned by the assignee of the present invention and herein incorporated by reference. In one embodiment of that device, peripherally disposed adhesive permits laminated joining of the wristband, while adhesive disposed at the longitudinally spaced contact portions permits a bonded connection therebetween.

While such prior art devices offer marked improvement in patient wristband accuracy and efficiency, there are situations where the relatively simple joining scheme between the two opposing ends of the band may be torn apart, thus negating the benefit of providing such notorious indicia. For example, if the patient is disoriented, or is operating under a defect of reason, he or she might become inclined to remove the wristband. Similarly, an inquisitive child can pick at the connection, causing it to come undone. In either event, if the wristband becomes separated from the patient, hospital personnel must perform time-consuming independent verification of the identity and medical needs of the patient prior to treatment to avoid potentially catastrophic consequences. One way to discourage wristband removal is to use a separate single-use clip, typically made from a metal or durable plastic, to keep the wristband in place. Such an approach is disadvantageous in that it requires separate storage and retrieval of both the wristband and the clip, and in some instances, the use of a special tool to crimp the clip to the wristband. This inconvenience to hospital personnel can lead to the consumption of extra time and money. Other methods can include the use of transparent plastic coverings that can be folded over onto the printed surface to improve water and tear-resistance. However, these too can add significant cost and complexity to the wristband.

Accordingly, there is a need for a wristband that can be easily formed from a sheet that is amenable to automated printing, and that upon wristband formation exhibits enhanced resistance to destruction and subsequent removal. There exists an additional need for such a wristband that does not sacrifice low cost, printability and ease of use to achieve these improved structural properties.

SUMMARY OF THE INVENTION

These needs are met by the present invention, which is directed to a wristband formed from a printer-compatible sheet. The sheet can come in either cut-sheet size, for individual or stacked feeding into a conventional printer tray, or in a continuous web, such as a Z-fold configuration, or in roll form which can be fed directly into a variety of printers, including mechanical impact, direct thermal, thermal transfer, ink jet, and laser printers. Multiple elongate strips can be placed on a single sheet. In the alternative, one or more labels, preferably as an array, can be similarly placed on the same surface of the sheet as the elongate strips, such that duplicate or related patient information can be printed onto the label array. The sheet is made up of at least a face ply adhesively joined to a liner ply, the latter of which can include a release coating placed on at least a part of the surface joining the face ply. Both the elongate strip and the labels can be die cut for ease of removal upon printing. The elongate strips have one or more detents (alternately referred to as wings) that extend from the strip such that the wings can be folded over to secure opposing strip contact portions once the strip is formed into a wristband, thus enhancing the durability of the connection.

According to one aspect of the present invention, an elongate strip configured to form a wristband is disclosed. The elongate strip includes a body portion defined by an inner surface and an outer surface, at least the latter of which is configured to accept printing (such as from a conventional automated printer, handwriting or other printing method) thereon, a pair of longitudinally spaced contact portions, each extending from the body portion such that they can be brought together to permit the strip to be shaped like a ring or bracelet, at least one laterally projecting detent (or wing) extending from at least one of the contact portions, and an adhesive layer disposed on at least one of the contact portions and the detent. The lateral edges define opposing side portions of the elongate strip, and extend substantially from one end of the strip to the other. As used in conjunction with the present disclosure, the term "substantially" refers to an arrangement of elements or features that, while in theory would be expected to exhibit exact correspondence or behavior, may, in practice embody something slightly less than exact. The one or more detents extend from the longitudinally spaced contact portions and include an inner surface and an outer surface. The adhesive on the longitudinally spaced contact portions is such that upon formation of the elongate strip into the wristband through looped contact of adjacent surfaces, a permanent bond is formed. Similarly, the adhesive layer disposed on the detent forms a permanent bond between the detent surface and whatever part of the wristband it comes in contact with, further strengthening the connection. In the present context, a contact portion need not be situated at the immediate end of the strip, and accordingly may include any portion of the adjacent strip structure that is configured to engage one or more surfaces of the opposing strip end or contact surface. As such, the contact portion may be disposed longitudinally inward from the end of the strip by such a distance as required to form a wristband of a size appropriate to the intended wearer. Accordingly, depending on the size of the strip and the nature of the engagement (i.e., whether a simple end-to-end contact or overlap, or a multilayer folded-back connection), the contact portion could extend longitudinally inward up to a significant part of the length between the immediate end surface and the strip midpoint. In the present context, the term "over" can include both direct adhesive contact between the detent and the connection (in the case of a single detent at each contact portion), as well as indirect contact with the connection through another detent (in the case of a detent set or pair disposed laterally across from one another at each contact portion).

Optionally, the adhesive layer disposed on the detent can be contiguous with the adhesive layer disposed on the contact portion from which the detent extends. Moreover, the detent is preferably integral with the elongate strip, such that both are made from a single piece of material. In addition, the detent can be part of a set of laterally projecting detents that can cooperate together to further secure the wristband. One or both of the detent sets (as well as an individual detent) can further be disposed longitudinally inward of the contact portion distal edge such that a tab is defined as extending longitudinally beyond the intersection formed between the longitudinal dimension of the elongate strip and the laterally projecting detent. The portion of the elongate strip inner surface that corresponds to the body portion can be free from adhesive to inhibit sticking between at least a portion of the inner surface and an adjacent surface, such as a wearer's wrist.

According to another aspect of the present invention, a self-adhesive wristband is disclosed. The wristband is formed from an elongate strip and at least one laterally projecting detent integrally formed with the elongate strip. The elongate strip includes a body portion, longitudinally spaced contact portions, an outer surface on the body portion upon which wearer-unique unique indicia may be printed, an inner surface opposite the outer surface, and an adhesive layer disposed on at least a portion of the body such that upon formation of the elongate strip into the wristband, the adhesive layer forms a first bond. The detent includes an adhesive and is configured such that once the first bond is made, the detent can be folded over an adjacent surface of at least one of the elongate strips to form an additional bond. Thus, when the longitudinally spaced contact portions are brought into looped contact with one another to establish adhesive contact between their respective adjacent surfaces, and subsequent connection is made between the adhesive layer disposed on the surface of the detent and at least one adjacent surface on the elongate strip, the wristband is further secured. Optionally, the detent is disposed adjacent at least one of the longitudinally spaced contact portions such that the formation of the adhesive bond is between the detent on the one longitudinally spaced contact portion and an opposing longitudinally spaced contact portion. In addition, the adhesive may be configured such that one or more of the adhesive bonds are permanent.

According to another aspect of the present invention, a form is disclosed. The form includes a face ply with at least one elongate strip defined therein, a liner ply disposed against the face ply, an adhesive disposed between at least a portion of the face and liner plies, and a release coating disposed between at least a portion of the face and liner plies to facilitate removable adhesion therebetween. The elongate strip is defined by a body portion and a pair of longitudinally spaced contact portions. As with the previous embodiments, the elongate strip includes an outer surface configured to receive printed indicia thereon and an inner surface opposite the outer surface. The elongate strip also includes at least one laterally projecting detent. At least a portion of the inner surface includes an adhesive layer such that upon connection of the pair of longitudinally spaced contact portions, at least a portion of the adhesive layer forms a bond therebetween. The detent is configured to adhesively fold onto the connection to form a bond therewith. The liner ply includes an inner surface, at least a portion of which is disposed such that it faces the inner surface of the elongate strip inner surface, and an outer surface. Optionally, the form is part of a continuous stack, which can be, for example, a Z-fold stack. The form could also be part of a continuous roll, or an individual cut sheet adapted to fit within a printer tray. Preferably, the form is configured to pass through a laser printer such that printed indicia may be placed on the printable outer surface of the elongate strip. The form may also include a plurality of labels disposed in the face ply, where the material of the elongate strip may be different than that of the labels.

According to still another aspect of the present invention, a form is disclosed. The form includes a face ply, liner ply, adhesive and release coating, where the face ply further comprises two portions, the first for one or more elongate strips formable into wristbands, and the second for one or more labels. The elongate strips are similar in construction to those of the previous embodiment, and as with the previous embodiment, may be made of a different material than the plurality of labels. The labels defined in the second portion of the face ply include an outer surface configured to receive printed indicia and an inner surface opposite the outer surface. The inner surface includes an adhesive layer to facilitate adhesive contact between the label and an object to be labelled. The liner ply is disposed against the face ply and includes an outer surface and an inner surface, at least a portion of which is disposed adjacent the elongate strip and label inner surfaces. The adhesive is disposed between at least a portion of the face and liner plies, as is the release coating. As with the previous embodiment, the form can be part of a continuous stack or roll, or could be an individual cut sheet. In practice, the plies of the form of the present invention are preferably assembled and then the face ply is printed in a single pass through a printer with the desired variable and nonvariable information. The elongate strip may then be detached from the form by peeling it from the liner ply and wrapping the band around a wearer's wrist to form a wristband. The wristband can then be secured at more than one location by means of the PSA on the longitudinally spaced contact portions and the one or more laterally projecting detents. The labels which remain on the form may be removed as needed and adhered to various surfaces. In the case of hospital use, these labels may be adhered to hospital forms, medicine containers, patient specimens or the like.

According to another aspect of the present invention, a method of making an adhesive strip to be used in the formation of a winged wristband is disclosed. The method includes adhesively combining at least a portion of a face ply to at least a portion of a liner ply to make a form, and defining in the face ply an elongate strip with longitudinally spaced contact portions. The elongate strip includes a first adhesive layer disposed on at least one of the contact portions and a second adhesive layer disposed on the detent. The ring-like structure of the wristband is formed with the first adhesive layer, while folding the detent over at least a portion of the elongate strip forms an additional adhesive bond to further reinforce the wristband. Optionally, the step of defining in the face ply an elongate strip includes providing a cut-out around a substantial entirety of the periphery of the elongate strip. This could include, by way of example, die cuts or perforations to facilitate peeling separation between the elongate strip and the liner ply, and between the elongate strip and extra material in the face ply. In addition, the first and second adhesive layers can be contiguously disposed. Such configuration could exist, for example, where the detent and one of the contact portions are adjacent one another. Another optional step could include feeding the form into a laser printer and printing indicia on at least the elongate strip.

According to yet another aspect of the present invention, a method of using a winged wristband is disclosed. The method includes configuring an elongate strip to include a body portion and a pair of longitudinally spaced contact portions, placing the elongate strip around a wearer's wrist, looping the elongate strip into a wristband shape, adhesively securing the longitudinally spaced contact portions to one another and folding at least one laterally projecting detent that is part of the elongate strip over a portion of the elongate strip such that the adhesive layer disposed on the detent forms a bond where the detent and strip contact one another. Optionally, the method comprises the additional step of printing indicia on the printable outer surface of the elongate strip prior to the step of placing the elongate strip adjacent a wearer's wrist. Preferably, the form containing the elongate strip is configured to be fed into a laser printer. Another option includes, prior to the step of folding the detent over a portion of the elongate strip, doubling back at least one of the longitudinally spaced contact portions so that the detent is adjacent the portion of the elongate strip that the detent is to be folded over.

According to still another aspect of the present invention, a method of using a wristband is disclosed. The method includes the steps of configuring an elongate strip to include the parts described in the previous aspect, placing the elongate strip adjacent a wearer's wrist, looping the elongate strip into a wristband shape such that a first adhesive bond is formed between a connection of the longitudinally spaced contact portions, doubling back the portions of elongate strip that are longitudinally distal of the contact point formed by the first adhesive bond along the outer surface of the body such that adhesive disposed adjacent a distal edge of one of the portions of the elongate strip forms a second adhesive bond with the outer surface of the body formed into the wristband shape, and folding the detent over the doubled back portion of the strip such that the adhesive layer disposed on the detent forms a third adhesive bond.

Other advantages and aspects of the present invention will become apparent upon reading the following description of the drawings in conjunction with the detailed description of the invention.

DETAILED DESCRIPTION OF THE PREFERRED EMBODIMENTS

Figure 1:
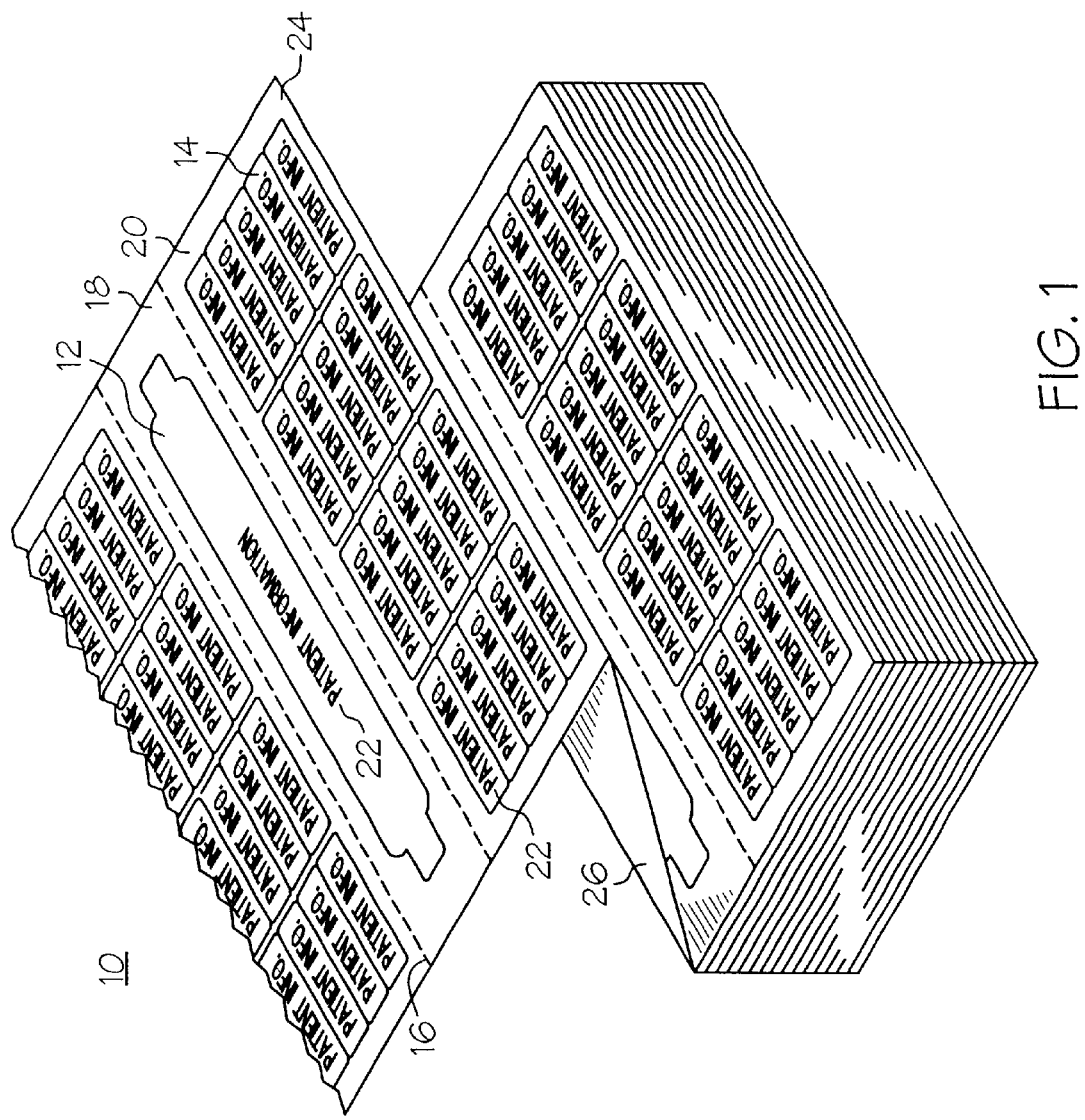
FIG. 1 is a perspective view of a stack of sheets that include an elongate strip formable into a wristband and an array of labels according to the prior art.

Referring first to FIG. 1, a stack of forms 10 according to the prior art is shown. Each form 10 includes a wristband 12 and a series of detachable labels 14, all of which may be removed along preferential lines of weakness. Each form 10 can be separated from adjacent forms along a line of weakness, shown in the figure as a perforation line 16. Each form 10 can be further subdivided into a first portion 18 which contains the wristband 12 and a second portion 20 which contains the labels 14. Indicia 22 may be printed on the surface of both the wristband 12 and the labels 14. The form 10 comprises a face ply 24 and a liner ply 26. The liner ply 26 can include a release coating on one surface to allow portions of the face ply 24 (particularly wristband 12 and label 14) to be peeled away from the liner ply 26 and then applied to various surfaces.

Figure 2B:
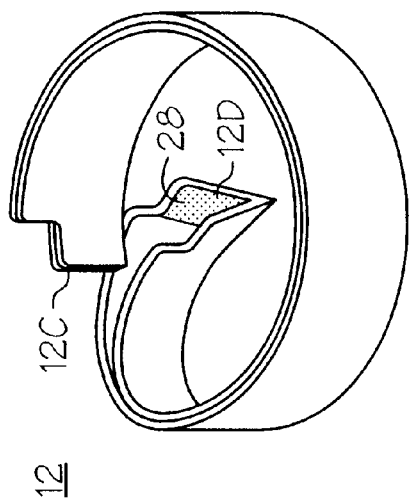
FIGS. 2A and 2B are perspective views of the formation of a wristband according to one embodiment of the device of FIG. 1.
Figure 2A:
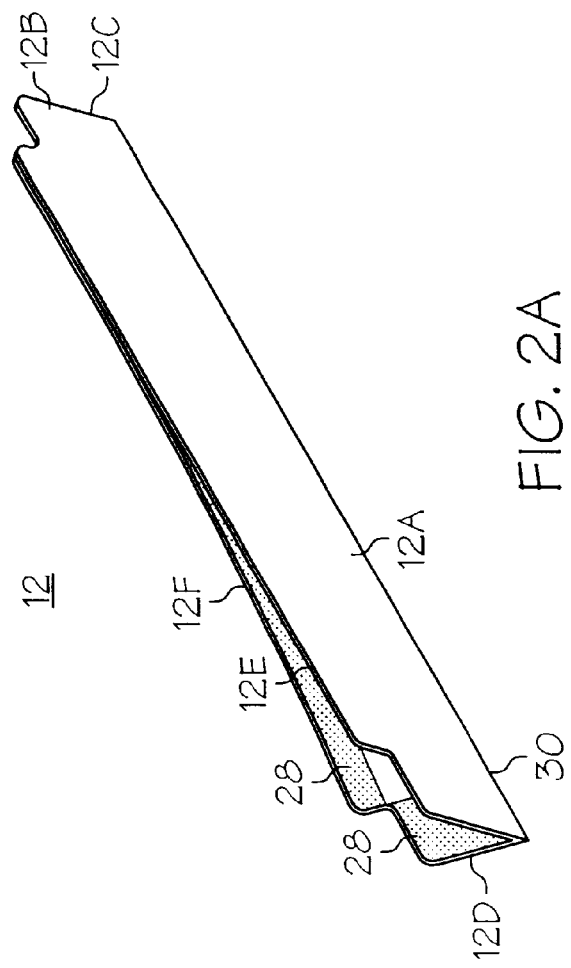

Referring next to FIGS. 2A and 2B, pressure sensitive adhesive 28 is included on a portion of the inner surface of wristband 12. Wristband 12 has a body portion 12A and end portions 12B. Remote, or distal, edges 12C and 12D and opposing lateral edges 12E and 12F, in conjunction with smaller lateral dimensions at the end portions 12B define the periphery of the wristband 12. The wristband 12 is folded lengthwise along fold line 30 to permit opposing lateral edges 12E and 12F to come in contact with one another. Upon folding, the pressure sensitive adhesive 28 along opposing surfaces across fold line 30 is brought into contact to form a bonded dual-layer laminate. The wristband 12 then now be looped over so that opposing end portions 12B can be brought into engagement with one another. One end (shown corresponding to distal edge 12D in the figure) must be kept slightly open to allow insertion of the other distal edge 12C such that upon subsequent pinching together of the surfaces divided along fold line 30, the adhesive 28 near distal edge 12D can bond with the end portion corresponding to distal edge 12C.

Figure 3B:
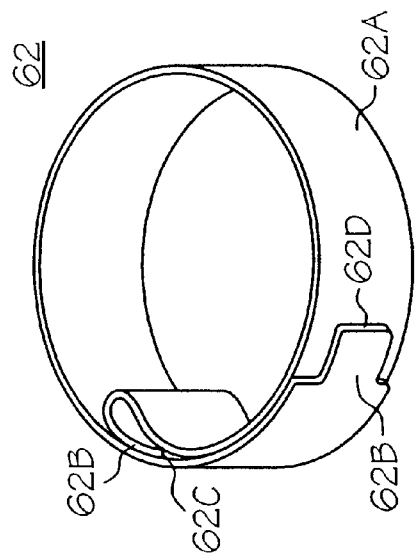
FIGS. 3A and 3B are perspective views of the formation of a wristband according to another embodiment of the device of FIG. 1.
Figure 3A:
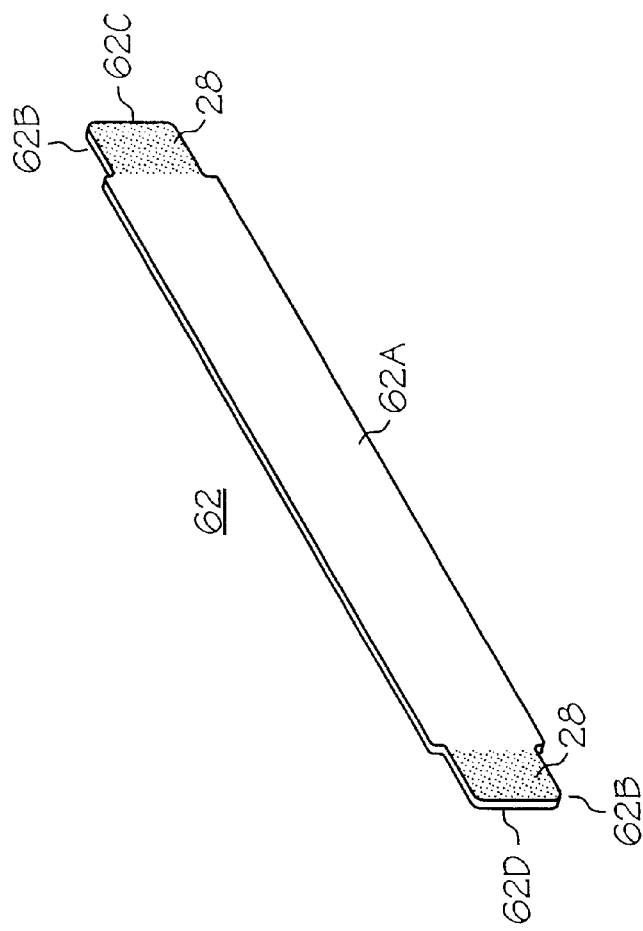

FIGS. 3A and 3B illustrate an alternate approach in the prior art. In this case, wristband 62 has a shape generally similar to that of wristband 12, except that it is not folded over onto itself. Adhesive 28 is placed on end portions 62B such that, upon looped formation of the wristband 62, as shown with particularity in FIG. 3B, the end portion 62B adjacent first distal edge 62C is folded back to contact an inner surface of body portion 62A. The end portion 62B adjacent second distal edge 62D is attached along body portion 62A with adhesive 28.

Figure 4:
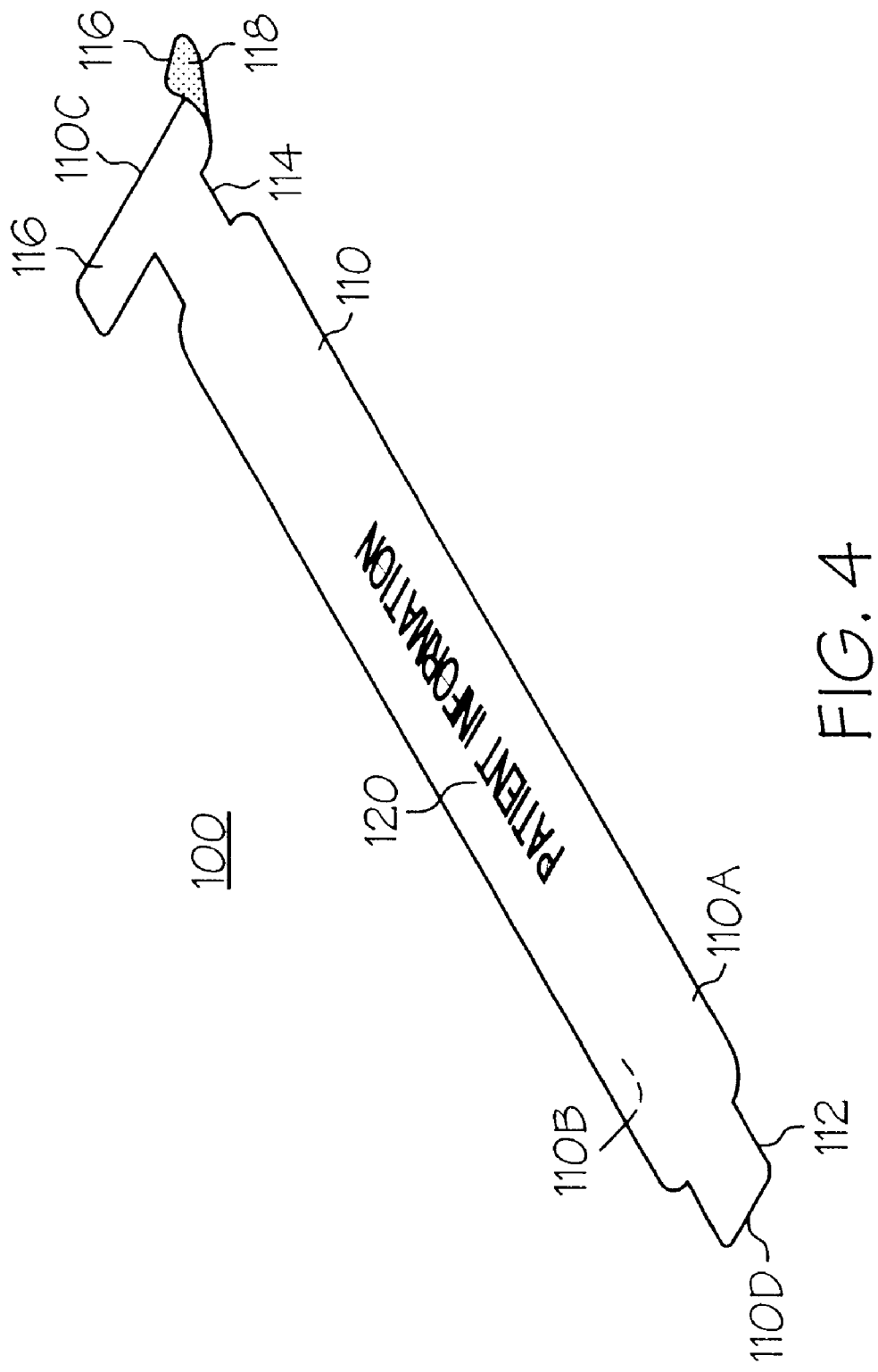
FIG. 4 is a perspective view of an elongate strip configured to be formed into a wristband according to an aspect of the present invention.
Figure 5:
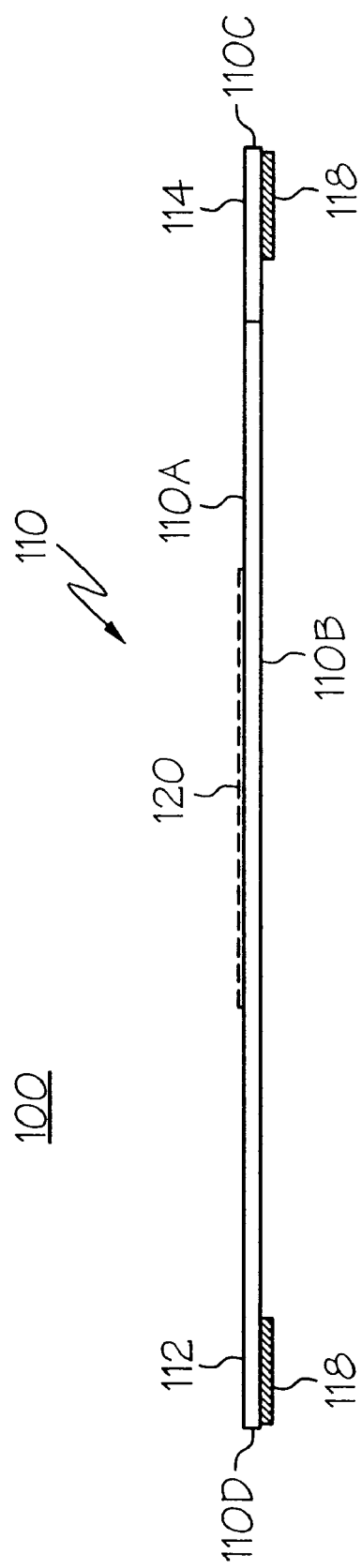
FIG. 5 is a side view of the elongate strip of FIG. 4, highlighting the placement of adhesive at various locations.

Referring next to FIGS. 4 and 5, an elongate strip 100 that can be formed into a wristband is shown. The material making up elongate strip 100 can be any material that readily accepts writing or printing, such as 0.002 inch thick white polyester film, or paper. Other viable materials include spun-bond polyolefins and polypropylene, examples of the former including KIMDURA™ or TYVEK™. Elongate strip 100 includes a body portion 110, which is further defined by an outer surface 110A and an inner surface 110B. In addition, elongate strip 100 includes a pair of longitudinally spaced contact portions 112, 114, a pair of laterally projecting detents 116 (also known as wings) extending from longitudinally spaced contact portion 114, and adhesive 118 disposed on the inner surface at detent 116. As shown with particularity in FIG. 5, adhesive 118 can optionally be disposed on both contact portions 112 and 114, both preferably facing the same way as inner surface 110B of body portion 110. While the contact portions 112, 114 are shown in FIG. 4 with a tapered, geometrically smaller footprint relative to the body portion 110, such features are not necessary to distinguish them from the body portion 110 to which they are attached. In addition, contact portions 112 and 114 can form extensions from body portion 110 such that the contact portions define a majority of the longitudinal surface of the elongate strip 100, rather than merely being confined to the ends (as shown in FIG. 4). Accordingly, additional adhesive (not shown) either contiguous with or separate from adhesive 118 can be disposed longitudinally inward along elongate strip 100 to augment adhesive bonding between opposing portions of elongate strip 100 that are brought into contact with one another during wristband formation. Printed indicia 120, such as patient information, can be printed on at least the outer surface 110A of the body portion 110. In addition to the embodiments shown in the present disclosure, it will be appreciated by those skilled in the art that the adhesive 118 may be included in a variety of locations and on either the inner or outer surface as desired. The detents 116 shown in FIG. 4, while preferably as a pair, could also define a single lateral projection such that there is only one detent 116. In the present disclosure, two detents are considered a pair when they extend from the same contact portion, such as contact portion 114 shown in the figure. The placement of adhesive 118 at one or both contact portions 112, 114 of elongate strip 100 ensures that when the strip 100 is looped around so that contact portions 112, 114 are brought together to form a wristband, a permanent bond is formed between them so that the wristband does not unwind. The placement of adhesive 118 on the detents 116 is such that once the wristband has been assembled by appropriate looping, the detents 116 can be folded over onto adjacent parts of the wristband, be that the elongate strip body portion 110, one of the contact portions 112, 114 or the other detent 116 in the case of a detent pair, to further strengthen the connection. Preferably, the detents 116 are integrally formed out of the same piece of material as the body portion 110 and contact portions 112 and 114 of the elongate strip 100, thus not only keeping manufacturing simple, but also increasing strength of the strip when formed into a wristband. As shown with particularity in FIG. 5, the adhesive can be disposed on both contact portions 112 and 114 to facilitate the joining of the opposing contact portions 112, 114.

Figure 6A:
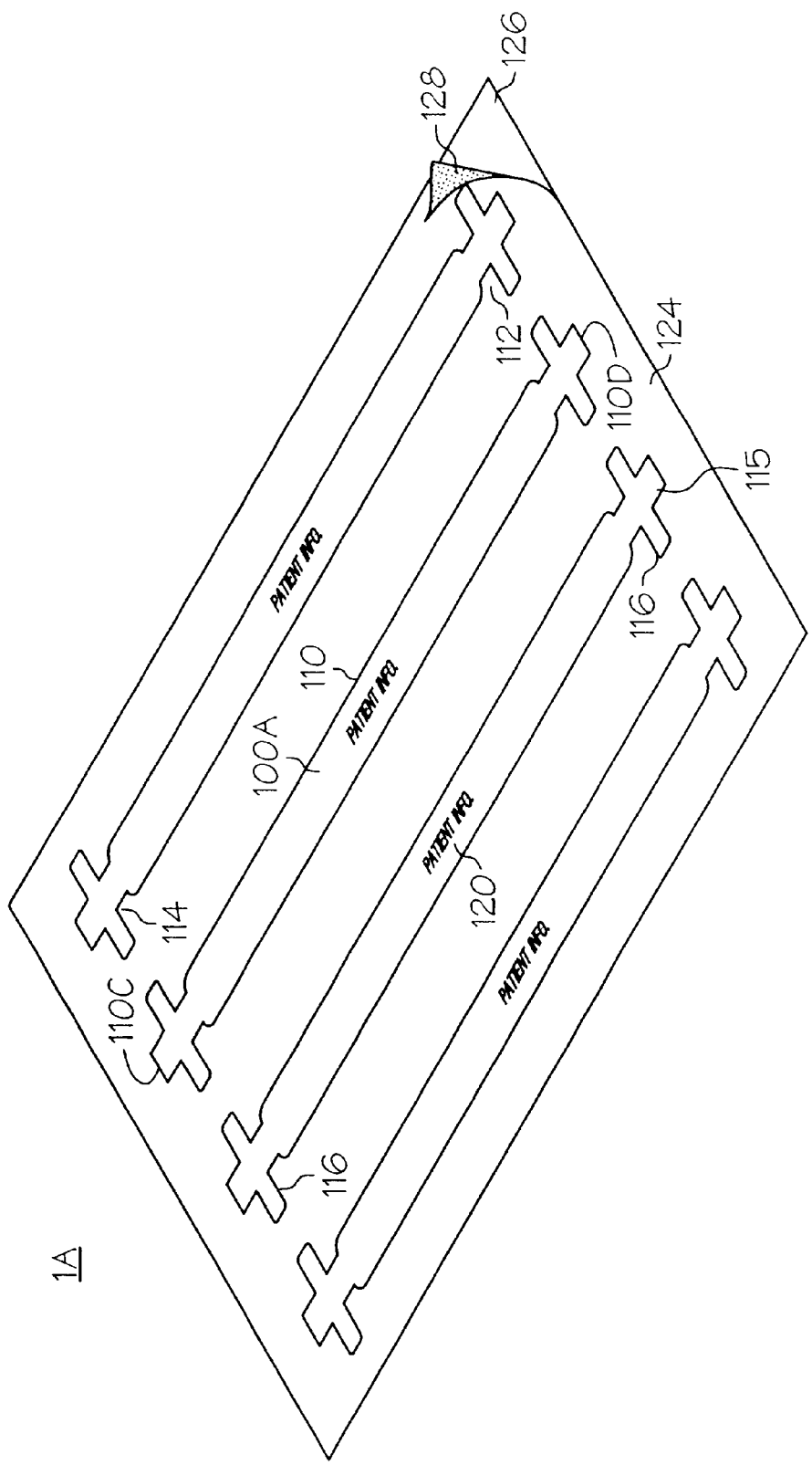
FIG. 6A is a perspective view of a single sheet form containing a plurality of elongate strips according to one embodiment of the present invention.
Figure 6B:
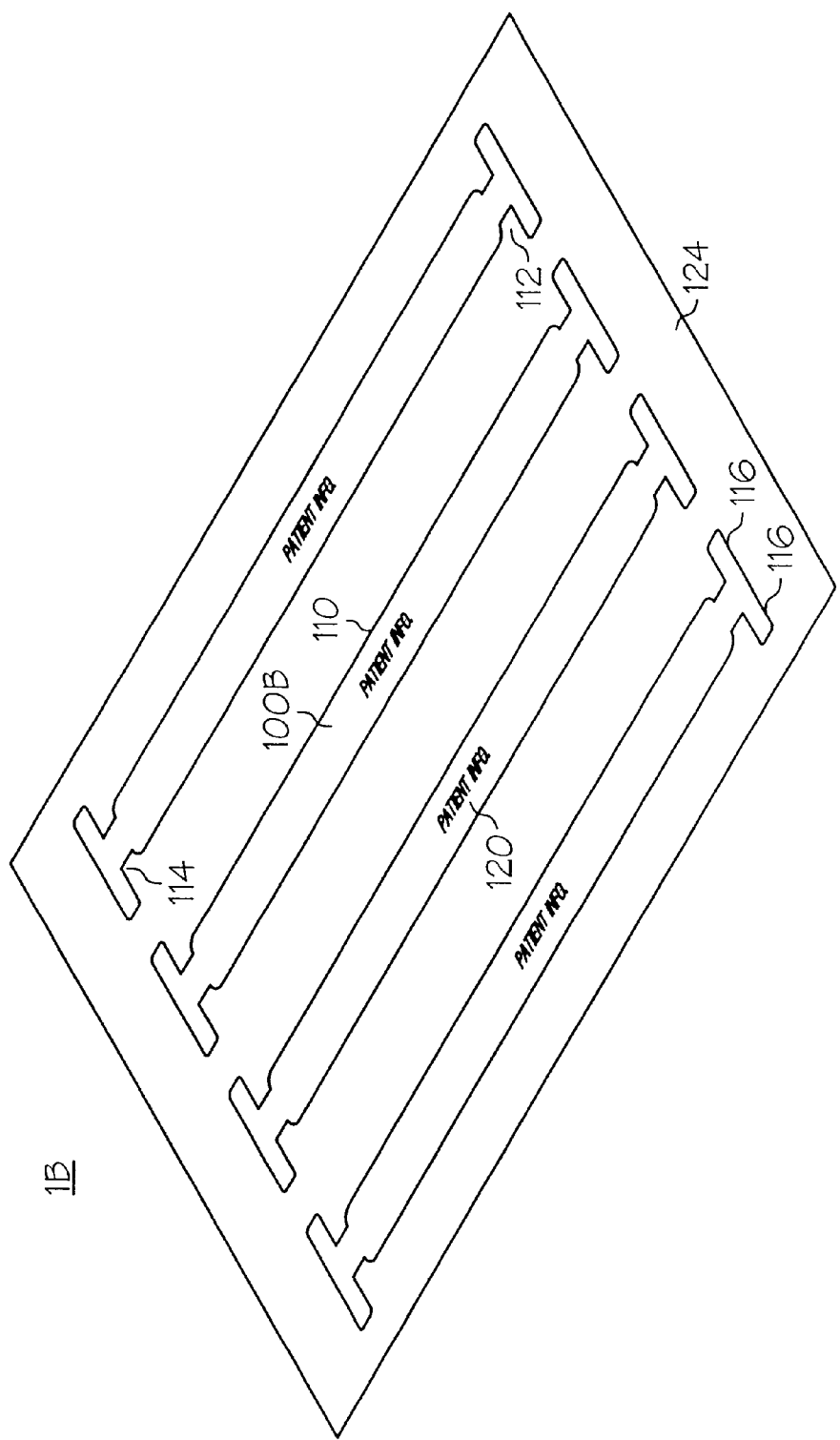
FIG. 6B is a perspective view of a single sheet form containing a plurality of elongate strips of the present invention that are formed in an alternative shape.
Figure 6C:
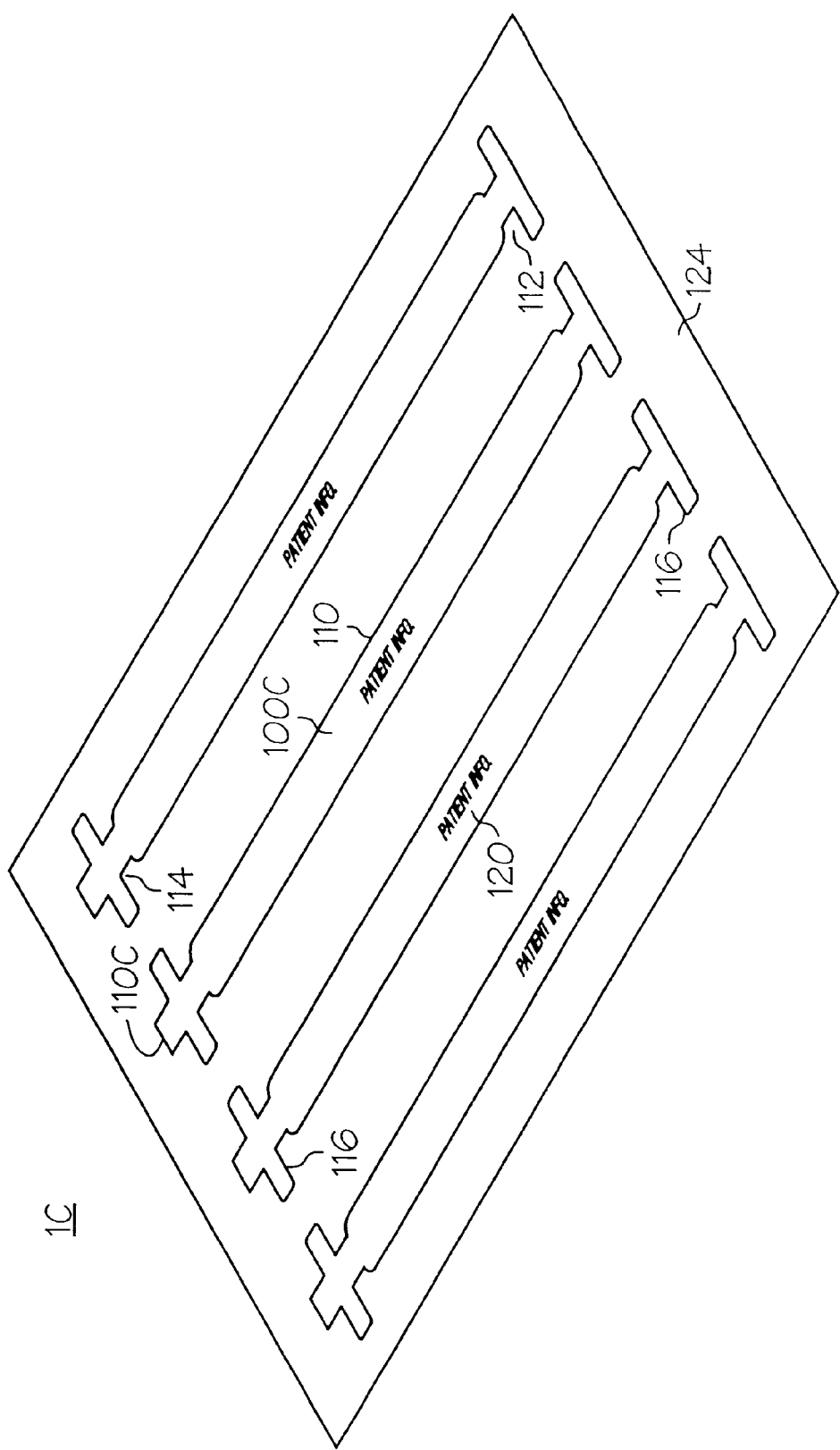
FIG. 6C is a perspective view of a single sheet form containing a plurality of elongate strips of the present invention that are formed in yet another alternative shape.

Referring next to FIGS. 6A–6D and 7, forms 1A, 1B, 1C and 1D, with respective multiple elongate strips 100A, 100B, 100C and 100D thereon, are shown. Although only depicted in FIG. 6A with a peeled-up corner to highlight the two-ply nature of the form 1A, the forms of all four figures include a face ply 124 with its inner face adhesively bonded to an inner face of underlying liner ply 126 via adhesive 128 disposed on the inner face of face ply 124. Preferably, liner ply 126 includes a layer of release coating (not shown) to facilitate removal of the individual elongate strips 100A. The release coating may be deposited in a pattern, such that it need not be present opposite portions of the inner face of face ply 124 that contain no adhesive 118 or 128, or it may occupy substantially the entire inner face of liner ply 126. In addition, the release coating may be deposited in a pattern such that some non-release coated portions of liner ply 126 are opposite adhesive coated portions of the inner face of face ply 124, forming a permanent bond therebetween. Adhesive 128 may be the same as adhesive 118, although it need not be. For example, while both are preferably of the class of adhesives known as pressure sensitive adhesives, one may be configured to form a permanent adhesive bond while the other forms a repositionable adhesive bond. Alternatively, both could be of the permanent or repositionable variety. Selective application of release coating (not shown) or patterned deposition of adhesive to leave adhesive-free regions can be used to promote bonding in certain parts of the form, while discouraging it in others (such as underneath the elongate strips so that the strips may be removed when needed). The shape of the elongate strips 100A in FIG. 6A is defined by a dual-T formation, one at each contact portion 112 and 114. Similarly, the shape in FIG. 6B defines an I-beam construction, while the shape of FIG. 6C is a combination of the structures shown in FIGS. 6A and 6B, and the shape of FIG. 6D includes a winged detent pair only at one contact portion 114 of the elongate strip. As shown with particularity in FIG. 6A, the dual-T shape is formed by having the detents 116 disposed longitudinally inward from the distal ends 110C and 110D. Under this construction, the remote part of the contact portions 112, 114 (which includes distal ends 110C and 110D) projects beyond the intersection between the detent pair and the longitudinal dimension of the elongate strip 100A to define a tab 115. The adhesive 118 formed on detent 116 can be contiguous with adhesive 118 formed on the tab 115 or other parts of the respective adjacent contact portion. Adhesive 118 used on elongate strips 100A, 100B, 100C and 100D can be the same as adhesive 128 used between the face and liner plies, although such is not required.

Figure 6D:
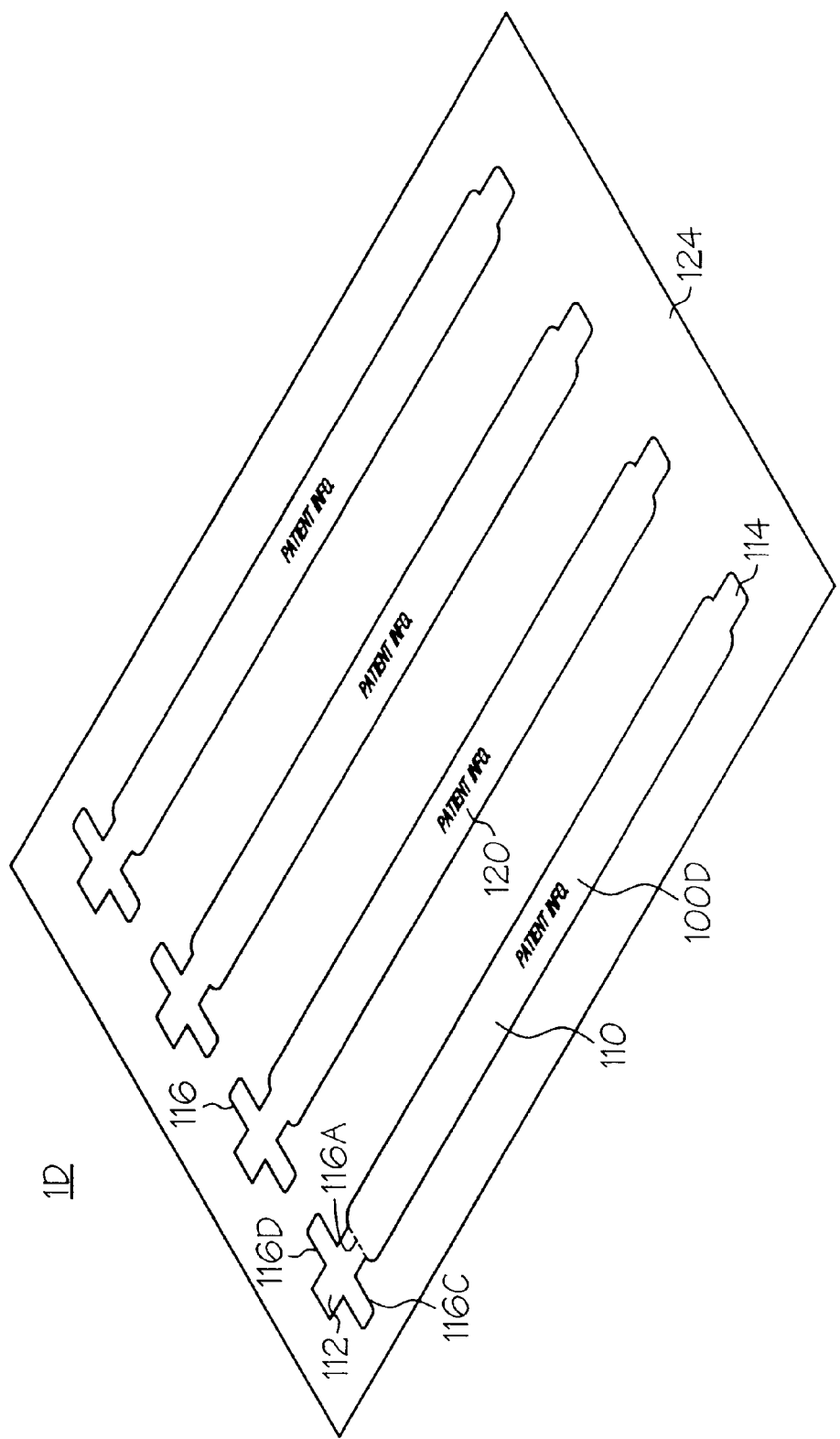
FIG. 6D is a perspective view of a single sheet form containing a plurality of elongate strips of the present invention that are formed in still another alternative shape.
Figure 7:
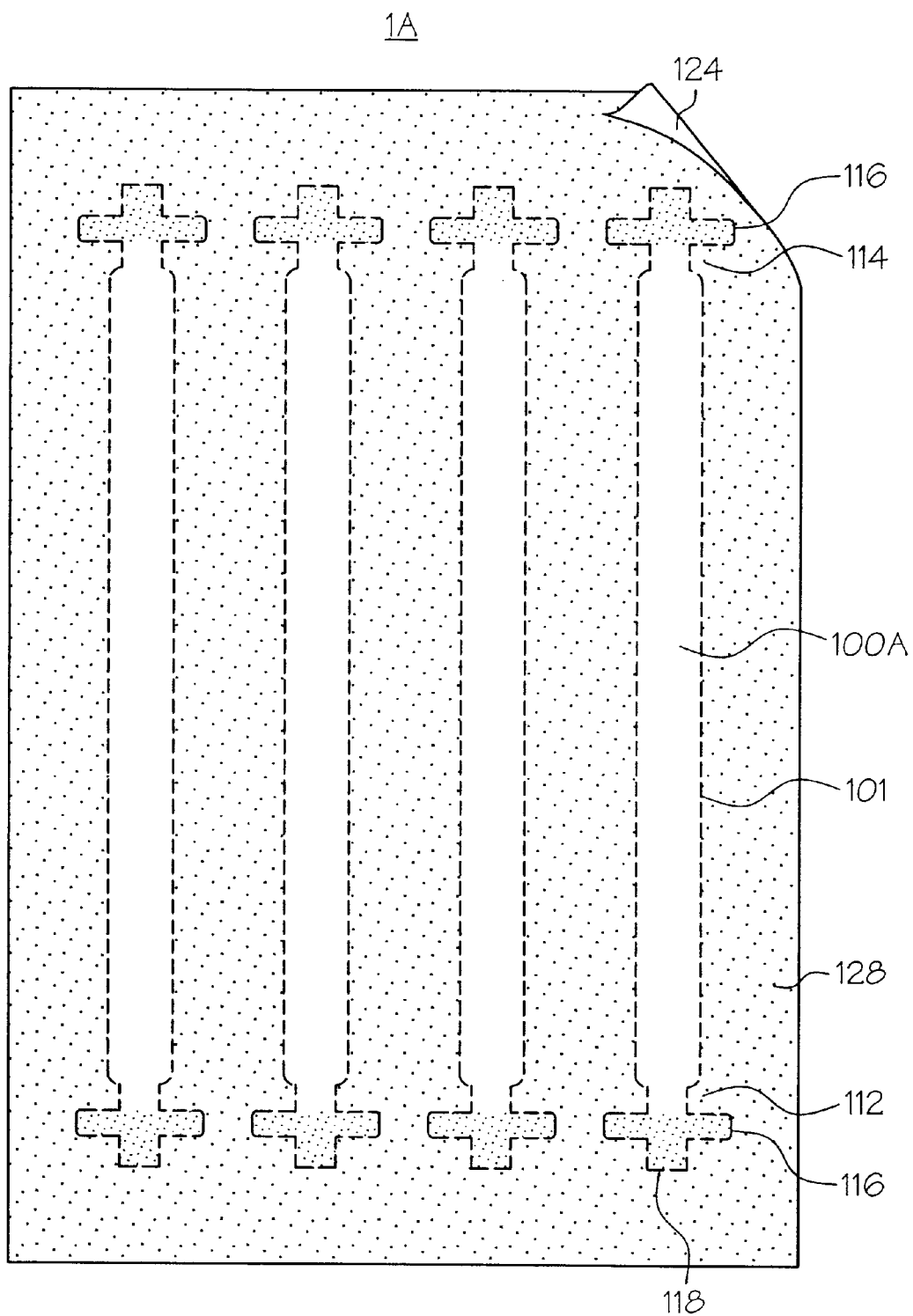
FIG. 7 is a view of the inner face of the face ply of the single sheet form of FIG. 6A.

The remaining shapes shown in FIGS. 6B through 6D are variations on the one depicted in FIG. 6A. Of these, the elongate strip 100D shape shown in FIG. 6D may be the simplest to manipulate, while those in FIGS. 6B and 6C (as well as FIG. 6A) can be used to make wristbands that possess additional structural capability through the multiple detent pairs. Referring with particularity to FIG. 7, the inner face of face ply 124 of form 1A is shown. Elongate strips 100A are shown with optional die cut lines 101. Adhesive 128 is disposed in a pattern over the substantial entirety of face ply 124 save portions of the elongate strips 100A that will, when formed into a wristband, contact the wearer's wrist. Adhesive 118 is disposed at both contact portions 112 and 114 such that it covers detents 116. Even though shown in the figure with both contact portions coated with adhesive 118, it will be appreciated, as previously discussed, that one of the contact portions may be left uncoated. In an alternate approach, a full-coat of pressure sensitive adhesive 128 could be applied over the entire face ply 124 such that die cuts 101 through the face ply 124 and liner ply 126 (not presently shown) define separation points. In this approach, since the die cuts 101 penetrate both plies, when an elongate strip 100A is removed from the form 1A, both the face and liner ply portions defined by the die cut 101 can remain together such that the substantial entirety of the face ply surface of the elongate strip 100A is coated with pressure sensitive adhesive 128 and covered with a removable liner (not shown). Additional die cuts (not shown) could be made in the portion of the liner ply that is defined by each elongate strip 100A so that discreet portions of the liner ply can be removed just prior to wristband formation. In one configuration, the additional die cuts made in the liner ply could be made adjacent contact portions 112 and 114 so that the liner ply covering those portions could be preferentially removed, thereby exposing only the pressure sensitive adhesive 128 on those portions, as the part of the liner ply that is proximal of the additional die cuts and facing the body portion of the face ply would remain adhered thereto. This would have the advantage of a simplified, less expensive adhesive coating step, yet would preserve adhesive-free contact between the body portion of the elongate strip and the wearer's wrist made possible by the continued presence of a part of the liner ply against the elongate strip.

Figure 8:
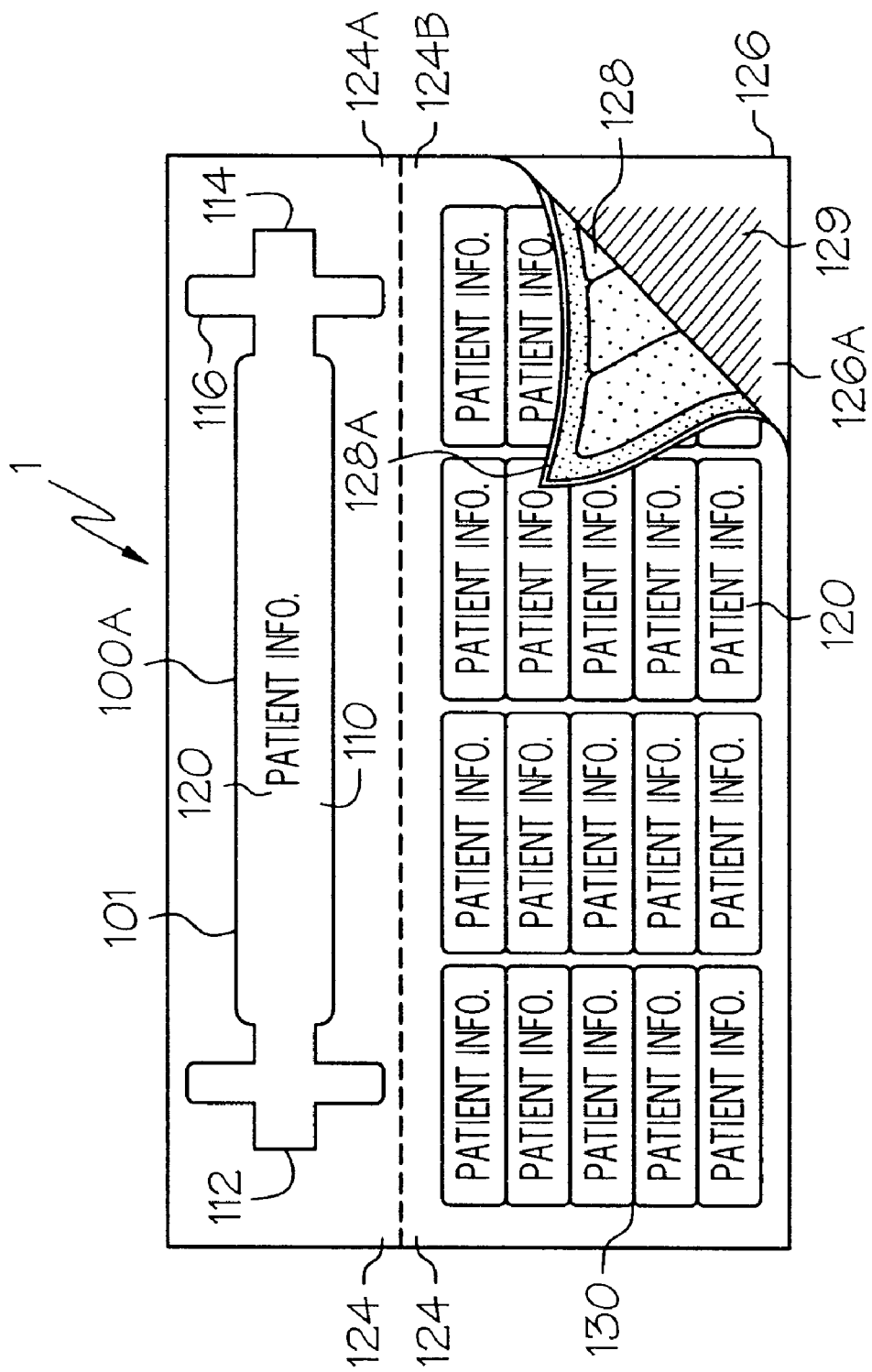
FIG. 8 is a top view of a form with both an elongate strip and an array of labels according to an alternate embodiment of the present invention.

Referring next to FIG. 8, a form 1 is shown with both an elongate strip 100A (similar to that of form 1A of FIG. 6A) formed in a first portion 124A of face ply 124 and a plurality of labels 130 formed in a second portion 124B of the face ply 124. Adhesive 118 (not presently shown) can be disposed on one or both contact portions 112, 114 and detents 116, while a complementary layer of release coating can be placed on the corresponding part of first portion 124A of face ply 124. The elongate strip 100A can be of the same material as labels 130, for example, paper. Preferably, elongate strip 100A is a different material, such as a tear-resistant polyester or the like. Similarly, first portion 124A of face ply 124 may be of the same material as second portion 124B of face ply 124, while in the alternate, first portion 124A may be of one material, such as, for example, a tear-resistant polyester or similar material, while the second portion 124B can be of another material, such as paper. Preferably, printed indicia 120 is correlated between the elongate strip 100A and the label 130. By way of a non-limiting example, in situations where the wristband wearer is a patient in a hospital or related health-care facility, the elongate strip 100A and label 130 may accept similar or complementary information all relating to the same patient such that the information may be placed upon, among other things, hospital documents, patient personal belongings and prescription, medication or specimen containers. The deposition of adhesive 128 between the face ply 124 and the liner ply 126 can take on various forms; in the version depicted in the figure, adhesive 128 can be disposed over the substantial entirety of the inner face of second portion 124B of face ply 124, leaving only a relatively narrow adhesive-free peripheral border 128A on face ply 124 to prevent adhesive ooze or spillover at the edge of form 1. Similarly, release coating 129 can be disposed on liner ply 126 such that it engages at least the adhesive 128 on the labels 130 to improve label 130 removability. A peripheral border 126A of liner ply 126 can be left free of release coating 129 so that the edges of face ply 124 remain adhered to the corresponding edges of liner ply 126. As previously discussed, adhesive 118 and 128 may be of the same or different composition, depending on user needs. Die cuts 101 around the periphery of the elongate strip 100A and the labels 130 can also be included to make easier their separation from the face ply 124. Alternatively, elongate strips 100B, 100C or 100D could be substituted for the dual-T shape of elongate strip 100A shown in the figure. The labels 130 on the form 1 may be removed and adhered as needed. It will be appreciated by those skilled in the art that the winged wristband of the present invention is not restricted to patient use, and accordingly may also find use in other applications, such as manufacturing facilities (to identify components), animal care facilities, plant nurseries or entertainment and recreation facilities, such as amusement parks, ski lifts or the like.

Figure 9:
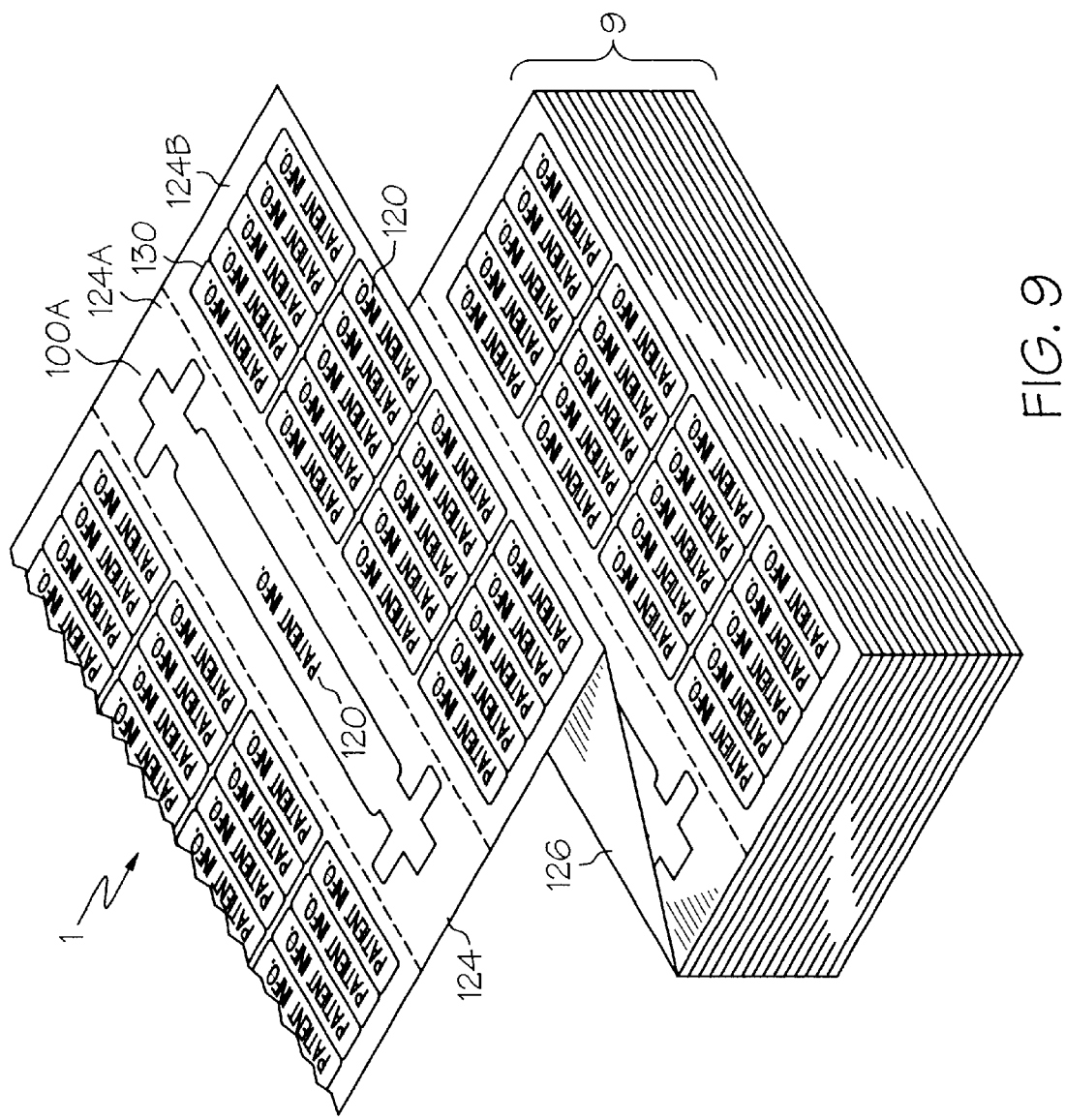
FIG. 9 is a perspective view of a continuous web of the forms of FIG. 8.

Referring next to FIG. 9, while the preferred form is a single cut sheet as shown in FIG. 8, the form 1 of the present invention may optionally be preferably produced as one of many in a continuous web 9 such as the Z-fold web shown or a roll (not shown). The continuous web may be fed through a printer in a single pass to add printed indicia 120 on both the elongate strip 100A and each of the labels 130 in the array of labels. The printed indicia 120 may include both variable information, such as dates, a patient's and attending physician's name, identification number and condition, and nonvariable information, such as the name of the treatment facility, emergency numbers or the like. The face ply 124 may be printed using a number of different automated printing devices including laser printers, ink jet printers, impact printers, ion deposition printers, thermal transfer printers and direct thermal printers. The forms 1 can be configured as individual cut sheets (as shown in FIG. 8) such that they can fit in the tray of a conventional printing device, such as the aforementioned laser printer. Similar to the discussion of FIG. 4, it will be appreciated by those skilled in the art that the arrangement of the elongate strip 100 and labels 130 on the form 1 may be varied without departing from the spirit of the present invention. By way of example, the form may include labels 130 of different sizes or of greater or fewer number, or different shapes for the elongate strips, such as 100B, 100C or 100D shown in FIGS. 6B, 6C and 6D, respectively. It is also possible that the placement of the elongate strips forming the wristband relative to the labels may be varied to accommodate specific user needs.

Figure 10B:
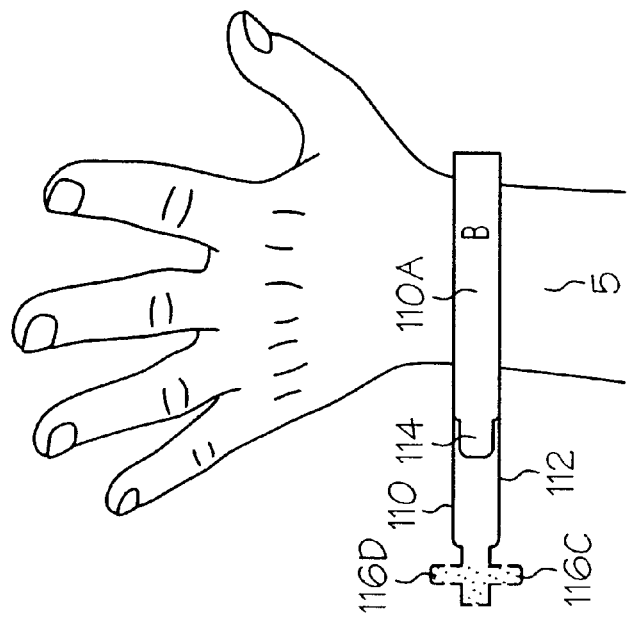
FIG. 10B is a top view illustrating how to affix a first contact portion of the wristband of FIG. 10A.
Figure 10A:
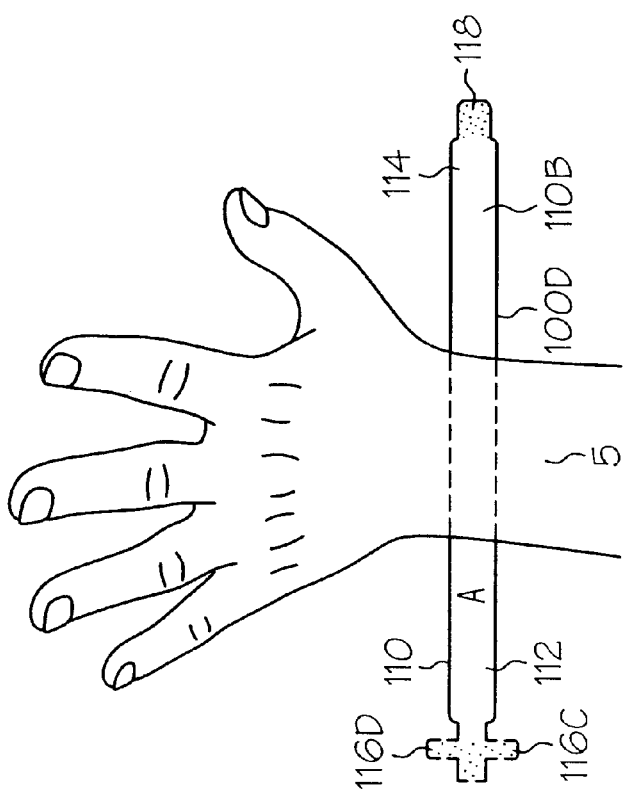
FIG. 10A is a top view illustrating how to loop a wristband of the present invention around a wearer's wrist just prior to securing the wristband.
Figure 10D:
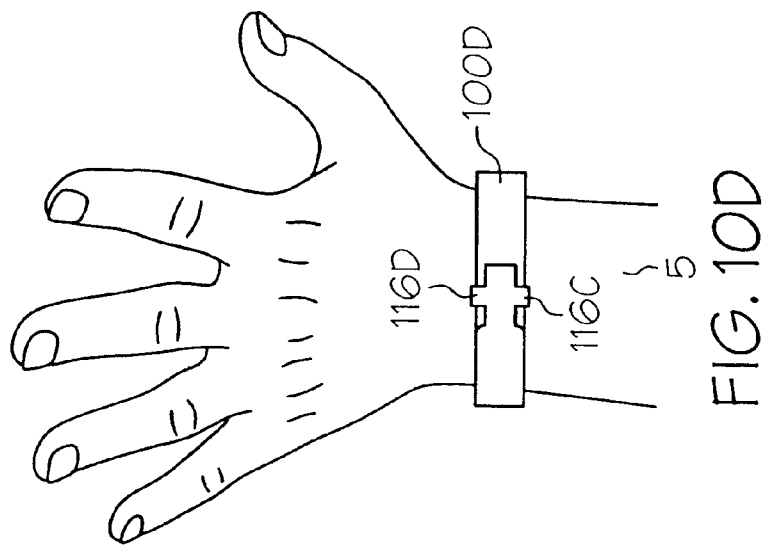
FIG. 10D is a top view illustrating the wristband of FIG. 10A affixed to a wearer's wrist.
Figure 10C:
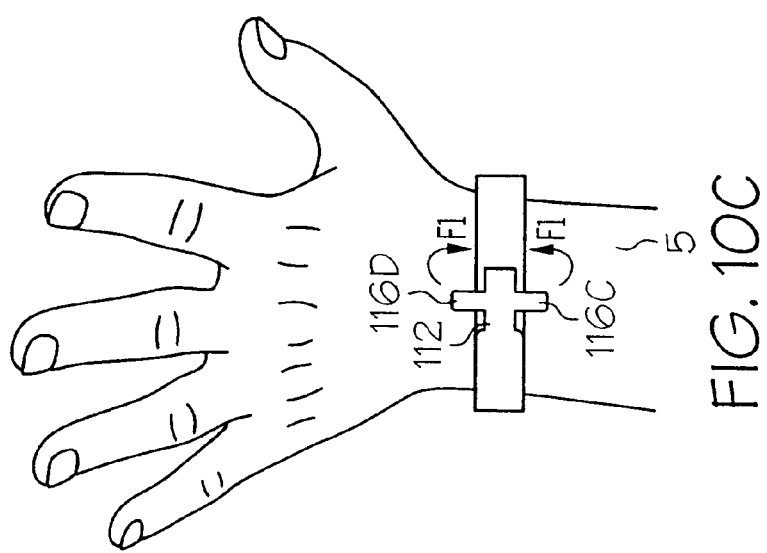
FIG. 10C is a top view illustrating how to fold back and affix a second contact portion of the wristband of FIG. 10A.

Referring next to FIGS. 10A–10D, an example fastening technique is shown. After the elongate strip 100D is peeled away from the form 1 (not presently shown), it is formed into a wristband and secured around the wearer's wrist 5 by the pressure sensitive adhesive 118 on one or both of the contact portions 112, 114 of the elongate strip 100D. Referring with particularity to FIGS. 10A and 10B, contact portion 112 with detents 116C and 116D and contact portion 114 are brought into overlapping relationship with one another such that adhesive 118 disposed on the inner surface of the elongate strip 100D at contact portion 114 is pressed against a surface of the adjoining location A to make a first adhesive bond. In FIG. 10B, once the first adhesive bond is made, contact portion 112 with detents 116C and 116D is folded over the wrist 5 such that exposed adhesive on contact portion 112 with detents 116C and 116D can be affixed to point B located on the outer surface 110A of body portion 110. In so doing, the first affixed region (corresponding to the step shown in FIG. 10A) typically doubles back on itself. Referring next to FIGS. 10C and 10D, after contact portion 112 is adhesively bonded at point B (no longer visible) to form a second adhesive bond, the elongate strip 100D (which is now in the shape of a wristband) is somewhat oversized relative to wrist 5. Detents 116C and 116D can be folded inward along fold directions F1 such that the adhesive 118 (no longer visible) forms a third adhesive bond with the inner surface 110B (not presently shown) of the elongate strip 100D that is facing the wearer's wrist. The doubling back and subsequent affixing depicted in FIGS. 10B–10D further strengthens the wristband through the second and third adhesive bonds. It will be appreciated by those skilled in the art that while the fastening technique of FIGS. 10–10D involves three separate bonding locations, a greater or fewer number are also encompassed by the present invention. For example, the adhesive forming the second adhesive bond discussed above could be left off such that only two adhesive bonds are formed; one by adhesive 118 disposed adjacent contact portion 114 and one formed by adhesive 118 disposed on the detents 116C, 116D.

Figure 11:
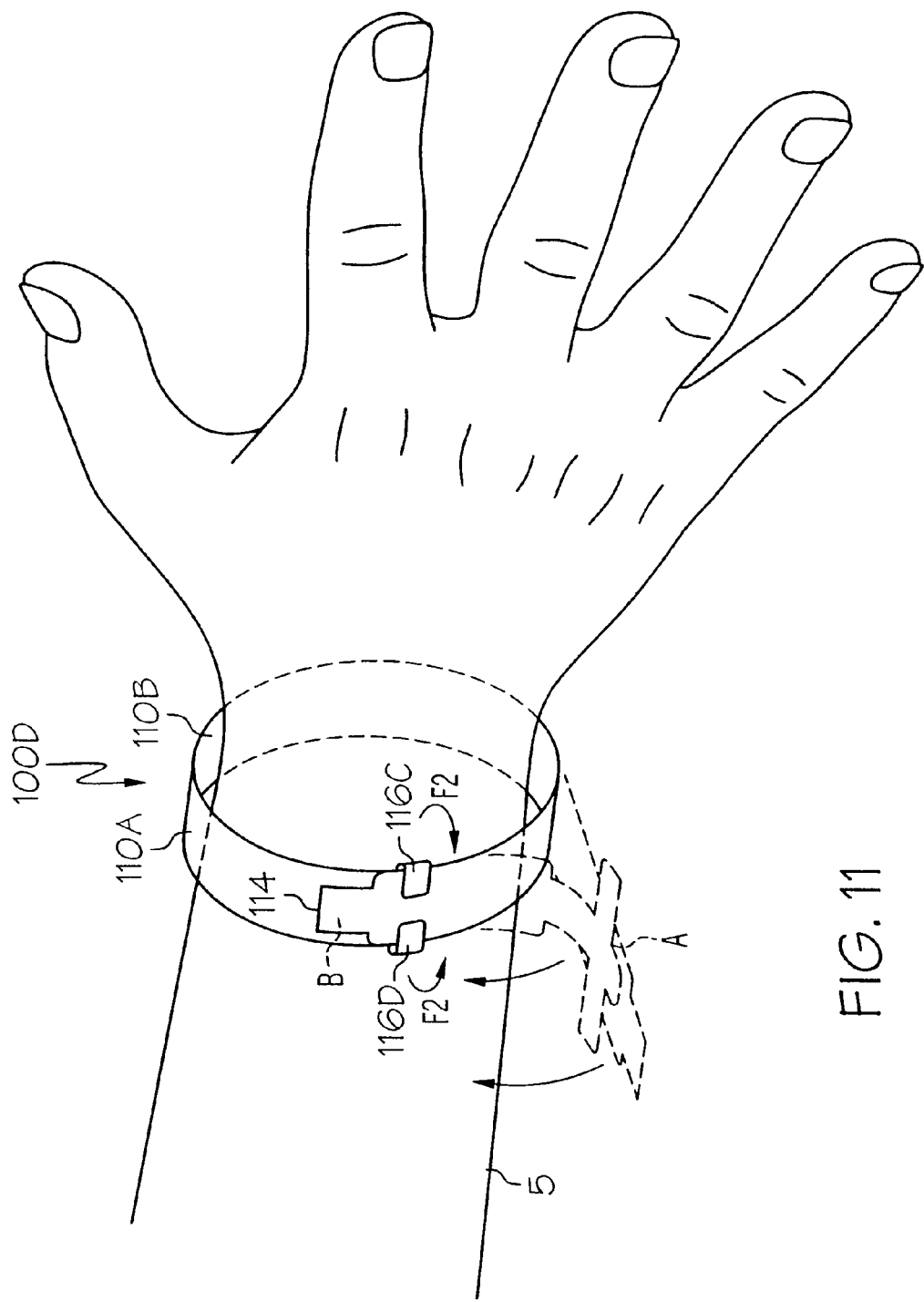
FIG. 11 is a perspective view illustrating a wristband of the present invention in an alternate way such that the detents fold outward in an affixed position on a wearer's wrist.

Referring next to FIG. 11, the strip 100D is shown in place around a wearer's wrist 5 by another fastening technique. In its as-affixed state, the wristband formed by elongate strip 100D has the detents 116C, 116D folded outwardly position along direction F2 to define a third adhesive bond, with dashed locations A and B showing first and second adhesive bond locations substantially similar to that of FIGS. 10A–10D. As before, the extra length of the elongate strip 100D has been taken up by the doubling back and subsequent adhering so that the as-fitted wristband is properly sized relative to the wearer's wrist 5. It will be appreciated by those skilled in the art that other fastening techniques utilizing the elongate strip 100D of the present invention abound. For example, a wristband can be formed by a straight overlap of contact portions 112 and 114 (without any doubling back at the adhesive bond) such that the detents 116C, 116D, which would be resident on the overlapping contact portion 112, can be folded inward towards the wrist so that they engage the inner surface 110B of the overlapped contact portion 114. Another technique may include affixing the ends of the elongate strip 100D together, face to face, such that the affixed ends form a flag. The detents 116C, 116D can be folded over to further secure the two ends to each other. While FIGS. 10A through 10D and 11 notionally show elongate strip 100D being formed into a wristband about a wearer's wrist, the use any of elongate strips 100A, 100B or 100C to achieve similar results is also contemplated.

Having described the invention in detail and by reference to preferred embodiments thereof, it will be apparent that modifications and variations are possible without departing from the scope of the invention defined in the appended claims.

We claim:

1. An elongate strip configured to form a wristband, said elongate strip comprising:
   a body with longitudinally spaced contact portions, said body having a printable outer surface and an inner surface opposite said outer surface;
   a laterally projecting detent extending from said elongate strip, said detent having an inner surface and an outer surface;
   an adhesive layer disposed on at least a part of at least one of said longitudinally spaced contact portions; and
   an adhesive layer disposed on said detent such that upon folding said detent over at least a portion of said elongate strip, adhesive contact is made therebetween.

2. An elongate strip according to claim 1, wherein said adhesive layer disposed on said detent is contiguous with said adhesive layer disposed on said respective longitudinally spaced contact portion from which said laterally projecting detent extends.

3. An elongate strip according to claim 1, wherein said detent is integral with said elongate strip.

4. An elongate strip according to claim 1, wherein said at least one laterally projecting detent is disposed longitudinally inward from said distal edge such that the part of said distal edge extending longitudinally beyond said laterally projecting detent defines a remote tab on said elongate strip.

5. An elongate strip according to claim 3, further comprising a pair of laterally projecting detents extending from said elongate strip.

6. An elongate strip according to claim 3, further comprising two pairs of laterally projecting detents, one pair extending from one of said pair of longitudinally spaced contact portions, and the other pair extending from the other of said pair of longitudinally spaced contact portions.

7. An elongate strip according to claim 6, wherein at least one of said pairs of detents is disposed longitudinally inward from said distal edge such that the part of said distal edge extending longitudinally beyond said pair of laterally projecting detents defines a remote tab on said elongate strip.

8. An elongate strip according to claim 7, wherein said adhesive layer on said contact portion and said adhesive layer on said detent are disposed on said inner surface.

9. An elongate strip according to claim 1, wherein the portion of said elongate strip inner surface disposed between said longitudinally spaced contact portions is free from adhesive.

10. An elongate strip according to claim 1, wherein said elongate strip is made from a tear-resistant material.

11. An elongate strip according to claim 10, wherein said tear-resistant material is polyester.

12. A self-adhesive wristband comprising:
   an elongate strip comprising:
      a body with longitudinally spaced contact portions;
      an outer surface on said body upon which wearer-unique indicia may be printed, and an inner surface opposite said outer surface; and
      an adhesive layer disposed on at least a portion of said body such that upon formation of said elongate strip into said wristband through connection of said longitudinally spaced contact portions, said adhesive layer forms a first adhesive bond therebetween; and
   at least one laterally projecting foldable detent integrally formed with said elongate strip, said detent including an adhesive layer disposed thereon such that upon formation of said first adhesive bond, said detent is configured to be folded over an adjacent surface of at least one of said longitudinally spaced contact surfaces to form a second adhesive bond.

13. A self-adhesive wristband according to claim 12, wherein said detent is disposed adjacent at least one of said longitudinally spaced contact portions.

14. A self-adhesive wristband according to claim 12, wherein said first adhesive bond is a permanent bond.

15. A self-adhesive wristband according to claim 12, wherein said second adhesive bond is a permanent bond.

16. A self-adhesive wristband according to claim 12, further comprising an adhesive layer disposed adjacent a distal portion of said elongate strip and configured to engage said outer surface of said body to form an adhesive bond therebetween.

17. A form comprising:
    a face ply with at least one elongate strip disposed therein, said elongate strip defined by a body with longitudinally spaced contact portions, said elongate strip comprising:
        a printable outer surface;
        an inner surface opposite said outer surface;
        a laterally projecting detent extending from at least one of said longitudinally spaced contact portions, said detent having an inner surface and an outer surface;
        an adhesive layer disposed on at least a part of at least one of said longitudinally spaced contact portions; and
        an adhesive layer disposed on said detent such that upon folding said detent over at least a portion of said elongate strip, adhesive contact is made therebetween;
    a liner ply disposed against said face ply, said liner ply including:
        an outer surface; and
        an inner surface, at least a portion of which is disposed facingly adjacent said inner surface of said elongate strip inner surface;
    an adhesive disposed between at least a portion of said face and liner plies; and
    a release coating disposed between at least a portion of said face and liner plies to facilitate removable adhesion therebetween.

18. A form according to claim 17, wherein said form is part of a continuous stack.

19. A form according to claim 17, wherein said form is part of a continuous roll.

20. A form according to claim 17, wherein said form is an individual cut sheet adapted to fit within a printer tray.

21. A form according to claim 17, wherein said form is configured to pass through a laser printer to accept printed indicia on at least said printable outer surface of said elongate strip.

22. A form according to claim 17, wherein said face ply further comprises a plurality of labels disposed therein.

23. A form according to claim 22, wherein said elongate strip is made from a different material than said plurality of labels.

24. A form according to claim 17, wherein said liner ply is coextensively disposed against said face ply.

25. A form comprising:
    a face ply comprising:
        a first portion with at least one elongate strip disposed therein, said elongate strip comprising:
            a body portion including a pair of longitudinally spaced contact portions, a pair of laterally spaced side portions, at least one laterally projecting foldable detent extending from at least one of said pair of laterally spaced side portions, an outer surface with at least a part of which is configured to receive printed indicia thereon, and an inner surface opposite said outer surface; and
            an adhesive layer disposed on at least a portion of said inner surface such that upon formation of a wristband from said elongate strip through looped connection of said pair of longitudinally spaced contact portions, at least a portion of said adhesive layer forms a bond therebetween and upon subsequent folding of said at least one laterally projecting foldable detent onto a portion of said wristband an additional adhesive bond is formed; and
        a second portion comprising at least one label disposed therein, said label including:
            an outer surface configured to receive printed indicia thereon, and an inner surface opposite said outer surface; and
            an adhesive layer disposed on said inner surface to facilitate adhesive contact between said label and an object to be labelled;
    a liner ply disposed against said face ply, said liner ply including:
        an outer surface; and
        an inner surface, at least a portion of which is disposed facingly adjacent said inner surface of said elongate strip inner surface;
    an adhesive disposed between at least a portion of said face and liner plies; and
    a release coating disposed between at least a portion of said face and liner plies to facilitate removable adhesion therebetween.

26. A form according to claim 25, wherein said liner ply is coextensively disposed against said face ply.

27. A method of making an adhesive strip to be used in the formation of a winged wristband, said method comprising:
    adhesively combining at least a portion of a face ply to at least a portion of liner ply; and
    defining in said face ply an elongate strip, said elongate strip comprising:
        a body with longitudinally spaced contact portions, said body having a printable outer surface and an inner surface opposite said outer surface;
        a laterally projecting detent extending from said elongate strip, said detent having an inner surface and an outer surface;
        a first adhesive layer disposed on at least a part of at least one of said longitudinally spaced contact portions; and
        a second adhesive layer disposed on said detent such that upon forming said wristband with said first adhesive layer, folding said detent over at least a portion of said elongate strip forms an additional adhesive bond.

28. A method according to claim 27, wherein said step of defining in said face ply an elongate strip includes providing a cut-out around a substantial entirety of the periphery of said elongate strip.

29. A method according to claim 27, wherein said elongate strip further comprises a pair of laterally projecting detents extending from at least one of said longitudinally spaced contact portions.

30. A method according to claim 29, wherein at least one of said pairs of detents is disposed longitudinally inward from a distal edge of said longitudinally spaced contact portion such that the part of said distal edge extending longitudinally beyond said laterally projecting detent defines a remote tab on said elongate strip.

31. A method according to claim 27, wherein said first adhesive layer and said second adhesive layer are contiguously disposed relative to one another.

32. A method according to claim 27, comprising the additional steps of:

feeding said form into a laser printer, and printing indicia on at least said elongate strip.

33. A method of using a wristband, comprising:

configuring an elongate strip to include:
- a body with longitudinally spaced contact portions, said body having a printable outer surface and an inner surface opposite said outer surface;
- a laterally projecting detent extending from said body, said detent having an inner surface and an outer surface;
- an adhesive layer disposed on at least a part of at least one of said longitudinally spaced contact portions; and
- an adhesive layer disposed on said detent;

placing said elongate strip adjacent a wearer's wrist;

looping said elongate strip into a wristband shape;

adhesively securing said pair of longitudinally spaced contact portions to one another; and folding said detent over a portion of said elongate strip such that said adhesive layer disposed on said detent forms a bond with said elongate strip.

34. A method of using a winged wristband according to claim 33, comprising the additional step of printing indicia on said printable outer surface of said elongate strip.

35. A method of using a winged wristband according to claim 33, wherein prior to said step of folding said detent over a portion of said elongate strip, said method comprises the additional step of doubling back at least one of said longitudinally spaced contact portions so that said detent is adjacent said portion of said elongate strip that said detent is to be folded over.

36. A method according to claim 33, wherein prior to said step of placing said elongate strip adjacent a wearer's wrist, said method comprises the additional steps of:

feeding said form into a laser printer, and printing indicia on at least said elongate strip.

37. A method of using a wristband, comprising:

configuring an elongate strip to include:
- a body with longitudinally spaced contact portions, said body having a printable outer surface and an inner surface opposite said outer surface;
- a laterally projecting detent extending from said elongate strip, said detent having an inner surface and an outer surface;
- an adhesive layer disposed on at least a part of at least one of said longitudinally spaced contact portions; and
- an adhesive layer disposed on said detent;

placing said elongate strip adjacent a wearer's wrist;

looping said elongate strip into a wristband shape such that a first adhesive bond is formed between said longitudinally spaced contact portions;

doubling back the portions of said elongate strip that are longitudinally distal of the contact point formed by said first adhesive bond along said outer surface of said body such that adhesive disposed adjacent a distal edge of one of the portions of said elongate strip forms a second adhesive bond with said outer surface of said body formed into said wristband shape; and folding said detent over said doubled back portion of said elongate strip such that said adhesive layer disposed on said detent forms a third adhesive bond.

\* \* \* \* \*

UNITED STATES PATENT AND TRADEMARK OFFICE
CERTIFICATE OF CORRECTION

PATENT NO. : 6,641,048 B1
DATED : November 4, 2003
INVENTOR(S) : Schintz et al.

It is certified that error appears in the above-identified patent and that said Letters Patent is hereby corrected as shown below:

Column 3,
Line 49, "wearer-unique unique indicia" should read -- wearer-unique indicia --

Column 9,
Line 34, "10OA" should read -- 100A -- .

Signed and Sealed this

First Day of June, 2004

JON W. DUDAS
*Acting Director of the United States Patent and Trademark Office*